United States Patent
Jongsma et al.

(10) Patent No.: US 7,431,458 B2
(45) Date of Patent: Oct. 7, 2008

(54) METHOD AND ARRANGEMENT FOR PERFORMING MEASUREMENTS OF THE TOPOGRAPHY OF A SURFACE BY MEANS OF A THERMAL EMISSION FROM THE SURFACE

(75) Inventors: Franciscus Hermanus Maria Jongsma, Ulestraten (NL); Johny De Brabander, Berg en Terblijt (NL)

(73) Assignee: Universiteit Maastricht, Maastricht (NL)

( * ) Notice: Subject to any disclaimer, the term of this patent is extended or adjusted under 35 U.S.C. 154(b) by 292 days.

(21) Appl. No.: 10/524,769

(22) PCT Filed: Aug. 6, 2003

(86) PCT No.: PCT/NL03/00566

§ 371 (c)(1),
(2), (4) Date: Sep. 8, 2005

(87) PCT Pub. No.: WO2004/016161

PCT Pub. Date: Feb. 26, 2004

(65) Prior Publication Data

US 2006/0103724 A1    May 18, 2006

(51) Int. Cl.
*A61B 3/10* (2006.01)

(52) U.S. Cl. .................................. 351/212; 351/214

(58) Field of Classification Search ............... 351/212, 351/200, 205, 211, 213, 214, 221
See application file for complete search history.

(56) References Cited

U.S. PATENT DOCUMENTS

| 6,024,449 A | 2/2000 | Smith |
| 2001/0046316 A1 | 11/2001 | Miyano et al. |

FOREIGN PATENT DOCUMENTS

| EP | 0 402 250 A | 12/1990 |
| WO | WO-93 14817 A | 8/1993 |
| WO | WO-94 07408 A | 4/1994 |
| WO | WO-02 45578 A | 6/2002 |

*Primary Examiner*—Huy Mai
*Assistant Examiner*—Jack Dinh
(74) *Attorney, Agent, or Firm*—Birch, Stewart, Kolasch & Birch, LLP (57) ABSTRACT

Method and arrangement for performing measurements of the topography of a surface (20), such as topography of an eye surface (20), wherein projecting means (1, 12) for projecting an image onto said surface (20) comprises a projection light source (1), and wherein at least a fraction of light leaving the surface (20) as a result of said projection is received using one or more receiving units (31, 32), such as charged coupled device (CCD) based cameras. The topography of the surface (20) is determined by analysis of said fraction of light leaving the surface (20), due to thermal emission and the image projected onto the surface (20) is projected with light comprising a colour for which the surface (20) is opaque, such as infrared light.

31 Claims, 5 Drawing Sheets

METHOD AND ARRANGEMENT FOR PERFORMING MEASUREMENTS OF THE TOPOGRAPHY OF A SURFACE BY MEANS OF A THERMAL EMISSION FROM THE SURFACE

FIELD OF THE INVENTION

The present invention relates to a method for performing measurements of a topography of a surface, such as the topography of an eye surface, wherein an image is projected onto said surface from at least one projection light source using projection means, wherein at least a fraction of light leaving the surface as a result of said projection is received using one or more receiving units, such as charged coupled device (CCD) based cameras, wherein measurement of said topography relates to surface mapping of said surface, wherein said topography of the surface is determined by analysis of said fraction of light leaving the surface, and wherein said fraction of light leaving the surface is comprised of light radiated by the surface due to thermal emission.

The invention further relates to an arrangement for performing measurements of the topography of a surface, such as topography of an eye surface, wherein measurement of said topography relates to surface mapping of said surface, said arrangement comprising projection means, which projection means comprise at least one projection light source for projecting an image onto the surface, further comprising one or more receiving units for receiving at least a fraction of light leaving the surface as a result of said projection, such as charged coupled device (CCD) based cameras, and means for analysis of said fraction of light leaving the surface for determining the topography of the surface.

BACKGROUND OF THE INVENTION

A method and arrangement of this type is for example disclosed in U.S. Pat. No. 6,024,449, wherein a grid pattern of pulsed monochromatic polarized light is projected onto a semi-difuse target surface, such as the de-epithelialized cornea of an eye undergoing photo refractive keratometry (PRK) or photo therapeutic keratometry (PTK), for performing high speed topography measurements on said target. In addition, the method and arrangement disclosed include respectively enable measurement of regions of overtemperature (hot spots) on the target surface using a quantum well infrared photodetector.

Many industrial, scientific and medical processes involve the measurement of the topography of surfaces for variety of applications. In most cases the accuracy of the measurements is of great importance for the quality of the output of the process mentioned. A specific type of surface topography measurements involves the measurements of curved surfaces, as is applied, for example, in ophthalmology where the topography of the corneal surface of the eye provides an indication of the quality of the eye and possible deflections from a healthy eye.

Some methods of measuring the topography of surfaces are based on specular reflection, e.g. a wave-front of a collimated coherent beam of light is projected on the surface and its reflected part is compared with an undisturbed reference beam (interferometric measurement) or a pattern is projected or mirrored by the surface and its reflection is compared with a reference pattern.

The limitations of these methods are that the accuracy is greatly reduced when both convex and concave curvatures are present on the surface or when rays are reflected outside the aperture of the sensor.

A solution is the application of moiré methods. Moiré methods are a versatile set of techniques for in-plane and out-of-plane deformation measurements, topographic contouring, and slope and curvature measurement. The basis of moiré methods are grids, which for use in eye surface topography may enable the projection of a pattern of lines onto the surface. Detection of the line pattern on the surface and overlaying the line pattern by an undisturbed reference pattern visualises the moiré pattern, which comprises the required information about the topography of the surface.

For detection of the projected pattern, a diffusely radiating surface is desired for this technique. For specular reflecting surfaces like the eye, in prior art, these surfaces are transformed in a diffusely radiating surface through the application of fluorescein on the surface. A diffuse reflection of the projected pattern can then be detected by the detection means.

A disadvantage of this technique is that it is marginally invasive. Especially for ophthalmologic purposes this is not desired since the application of fluorescein onto the eye disturbs the tear film and makes it difficult to see references, such as the pupil or the iris, on or beneath the surface of the eye. Another drawback of this technique is that it does not work on dry surfaces, such as dry eyes.

A good example of a method and arrangement used for eye topography, wherein a derivative of moiré methods and the application of fluorescein is used, is described in European patent EP 0 551 955. This document describes some features of such a kind of imaging in surface topography measurements, especially in relation to eye and corneal surface topography, in more detail.

International patent application no. WO 02/45578 is directed to a method for determining the topography of a surface of a biological tissue, comprising the projection of an image onto this surface. The projection is performed with either ultra-violet (UV) or infra-red (IR) light. The method comprises measurement of scattered radiation from the surface as a result of said projection. The method also proposes the use of a thin fluorescent layer for increasing the yield of light to be measured. If UV light is used for determining the topography of the surface, the method may be based on autofluorescence of the surface.

As mentioned above, the use of a fluorescent layer may not always be desired, especially not in application directed to determining the topography of a corneal surface as the fluorescein disturbs the tear film on said surface. Disadvantages of the use of UV light, especially in the range for which autofluorescence occurs, is that at these frequencies a surface such as an eye surface may be damaged due to protein denaturation, which may cause actinic conjunctivitis. If neither a fluorescent film nor UV light is used, but instead the method is only based on analysis of scattered radiation from the surface alone using IR light, the yield of light to be analysed may be very small, since the particles that are to scatter the radiation back, are for a large part smaller than the wavelength used. A person skilled in the art may appreciate that such a scattering process will be inefficient.

SUMMARY OF THE INVENTION

It is an object of the present invention to provide a method and arrangement for performing measurements of the topography of a; surface, such as an eye or corneal surface, which alleviates the problems described above and wherein the surface remains undisturbed, thus reducing the chance of disturbing measuring results by the measuring method itself.

These and other objects and advantages achieved by the present invention in that there is provided a method as described in claim 1.

Projecting the image using, for example, infra-red light provides several benefits. For this colour the eye is not only fully opaque, but the photons that are absorbed by, for instance, a tissue are converted into heat. This heat causes thermal excitation of the matter in the tissue generating radiation comprising wavelengths other than the original wavelength that was projected onto the surface. The light that is not absorbed by the tissue, but may instead be reflected back to the receiving unit (specular reflection, scattering), is still comprised of its original wavelength. This natural process enables filtering of the reflected light from the signal by for example an optical filter or dichroic mirror, leaving only the fraction of light caused by thermal emission to be detected by the detection means. It will be appreciated that this latter fraction comes from the diffusely radiating surface, and provide the diffuse image that can be used in surface mapping methods. This method may in particular be efficient if mid-IR light is used, since the thermally emitted fraction is relatively large for these frequencies. Note further that invention is not limited to the use of mid-IR since other wavelengths may be used for different surfaces than the corneal surface taken here as an example.

According to an embodiment of the present invention, the image projected onto the surface is projected with light comprising a colour for which the surface is opaque.

The advantage of using light of such a colour is that this illumination can be applied to eyes with a normal tear film as well as dry eyes and dry surfaces, whereas methods of prior art, such as methods using the application of fluorescent substances on the corneal surface, cannot be used in dry eyes. In addition, the eye will not register the light used to perform the measurements and hence it will be disturbed by the measurement. Both the eye, as well as the results of the measurement are undisturbed by the way of measuring. Also, due to the transmission and scattering properties of the different tissues present in the eye, under the right conditions only the shape of the outer corneal epithelium and conjunctiva are mapped.

In an embodiment of the invention an ambient light source is used to enable detection of references on the surface using one or more receiving units. The ambient light source may radiate light of a colour for which the surface is at least partly transparent, for instance in order to reveal structures and references that are present directly underneath the surface.

In a preferred embodiment the light radiated by the ambient light source is near-infrared (near-IR) light (wave length $\lambda < 1,3$ µm) and the surface is a corneal surface of an eye.

The advantage of the above used ambient light source and in particularly the near-IR light source that is used in corneal surface topography is the revelation of structures underneath the surface, such as the pupil or the iris of the eye. When the pupil is visible, it can serve as a distinct landmark for alignment after the measurement. For this purpose it is necessary that contraction of the pupil can be controlled by the operator of the measuring device. By using near-IR light in combination with the invention, the pupil is not influenced by the measuring light nor the ambient light source, and references are revealed without introducing disturbances. The operator may, for example, control dynamics of the measured subject, such as contraction of the pupil, using other methods, for instance the use of an additional (visible) light source in combination with the invention.

In another embodiment of the invention the fraction of light leaving the surface is received by a plurality of receiving units. In this embodiment, the receiving units have been accurately focused, magnified and aligned for the purpose of receiving a suitable image of sufficient quality at a preset distance. Said embodiment may, for example, be arranged to measure the surface topography of a surface located at a predetermined distance from the front of the measuring arrangement (since it may be a curved surface, the distance meant here is the average distance). The surface of the object to be measured may be fixed in space, while the arrangement may be (slightly) moveable, or vice versa.

In the above mentioned arrangement, the surface to be measured has to be brought in position, relative to the arrangement, such that (on average) it coincides with the 'plane of focus' of the arrangement. The arrangement may therefore be equipped with means for adjusting the position relative to that of a surface to be measured.

For adjusting, the embodiment comprises means for projecting references onto the surface and at least some of the projection angles of the projected references are different from each other. The references are projected such that they form an easy recognisable pattern in the 'plane of focus'. In addition, the angles of projection are such that in any plane, parallel to said 'plane of focus' but at a small distance spaced apart thereof, the pattern formed by the references is recognisably different.

By adjusting the position of the arrangement relative to the position of the surface, one can easily establish the distance for which the surface coincides (on average) with the 'plane of focus', by evaluating the pattern formed by said references.

The triangulation method described above can be summarized by the following steps: projecting a plurality of references onto the surface with at least partially different projection angles such that a known pattern is formed by the references if projected on the 'plane of focus', adjusting the distance between object and arrangement as to approximate to the desired pattern as close as possible.

In a preferred embodiment near-IR light is used for projecting the references used for triangulation or, when the surface is an eye surface comprising a corneal surface to be measured, the references may be projected onto a region outside the pupil, such as the conjunctiva.

By focussing on the conjunctiva adjacent to the corneal tissue no visible light load for the patient is present. By using near-IR light the chances of response of the eye to the focussing are further reduced.

In a specific embodiment the projected image of a grid is flashed onto the surface, and the receiving units are synchronised with this flash.

The advantages of flashing the image onto the surface is that movement artefacts are frozen by the flash.

In another embodiment a series of flashes is projected onto the surface enabling determination of dynamics of the topography of the surface.

In an other embodiment of the invention the emission component is separated from the excitation component of the light, and the excitation component of the light is used to synchronize the receiving units with a flashed projection.

Note that specular reflection component of the light may be suppressed by the use of crossed polarizing optics, for instance by a vertical oriented polarizer placed in the projector and a horizontal oriented polarizer near the receiving unit. Note that the thermally emitted fraction of light, used in the analysis of the topography will not be affected by the polarisation filter.

For safety purposes it should be noted here that the use of UV light may, for specific use of the invention for corneal surface topography measurement, damage the corneal surface as it may affect protein structures in the corneal tissue. Although dependent on the application of the invention, use of the invention with UV light is not ruled out, for use on corneal surfaces it is however not advised.

It will be appreciated that the projected pattern may be created by a variety of means other than grids. A slid or a double slid or any other interferometric technique may be used to create an interference pattern suitable for grid projection methods. In a certain embodiment the interference pattern used is a sinus-shaped fringe pattern.

The invention is not limited to the use in grid projection or moiré methods. The principle of using light for which the surface is opaque is advantageous in many other techniques wherein optics are used to determine the topography of a surface. The use of this invention for similar purposes may be suggested by the additional advantages of the use of the invention for ophthalmologic purposes as described above. The invention is not limited to the use of IR or UV light, or similar colours. It will be appreciated that, in relation to surface topography, the concept of adapting the wavelength of light or radiation to the characteristics of the measured subject is widely applicable in a variety of cases, especially for medical purposes. Examples are fluorescent angiography as used for retinal blood flow measurement or technical purposes such as for aspheric (contact) lenses.

The above-mentioned and other features and advantages of the invention are illustrated in the following description of some embodiments of the present invention, with reference to the enclosed drawings. Systems arranged for deploying above-mentioned method are regarded as an embodiment of the present invention.

DETAILED DESCRIPTION OF THE EMBODIMENTS

Figure 1:
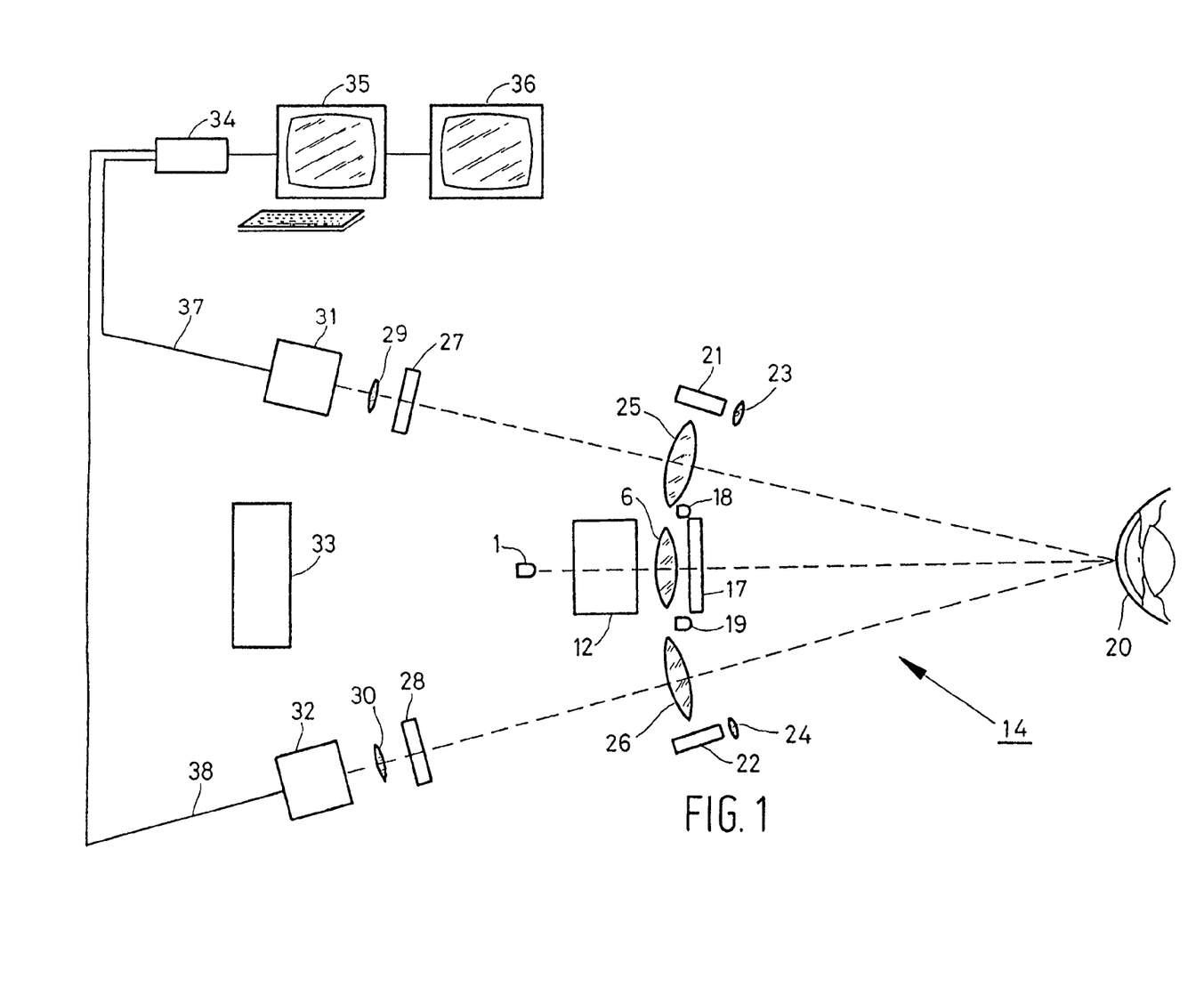
FIG. 1 shows a schematic top view of an arrangement according to the present invention.
Figure 2:
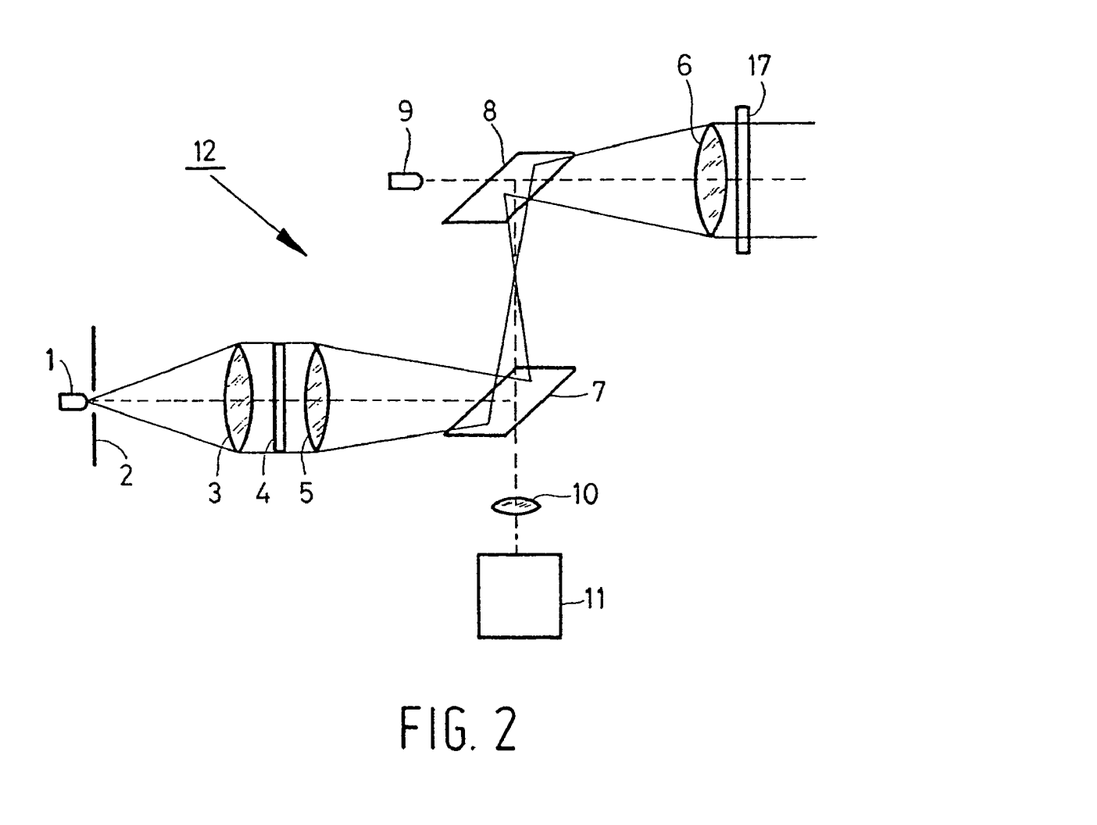
FIG. 2 shows a schematic side view of the projection unit of the arrangement of FIG. 1.

An arrangement 14 according to the present invention is shown in FIGS. 1 and 2. The arrangement has three main functions: projection of a line pattern on the corneal surface 20, triangulation focussing, and visualisation of references by using ambient light sources 18 and 19. FIG. 1 shows a schematic top view of the arrangement, and FIG. 2 shows a side view of the projection unit generally indicated as 12.

Projection on the surface is performed by generating a line pattern projection through light source 1, aperture 2, lens 3, grid 4, telecentric lens 5, (dichroic) mirrors 7 and 8, and telecentric lens 6. The image leaving telecentric lens 6 is projected onto the corneal surface 20. The diffuse image of the grid 4 on the corneal surface 20 is picked up through telecentric lenses 25 and 26, filters 27 and 28, telecentric lenses 29 and 30 and cameras 31 and 32. The signal of cameras 31 and 32 is transmitted via lines 37 and 38 to frame grabber 34 and further processed by PC 35, after which it is visualised on monitor 36. Aperture 2 may be a 3 mm wide slid. Grid 4 may comprise the sinus-shaped line pattern with a line density of about 3 lp/mm (line pairs per millimetre), which lines run at right angles through the projection axis. Mirrors 7 and 8 are dichroic mirrors that reflect the light coming from projection light source 1. Filters 27 and 28, in the optical path between cameras 31 and 32 and eye 20, are added to block the light caused by specular reflection of the projected image. In the case that projection light source 1 is a mid-IR light source, only the diffuse image caused by thermal radiation due to the absorbed IR radiation by the tissue, should be recorded by cameras 31 and 32. The light caused by thermal radiation typically has an other wave length than the light caused by specular reflection. The light caused by specular reflection is of the same wave length as the light coming from the projection source, and can thus be filtered out easily by filters 27 and 28.

Frame grabber 34 subsequently captures the frames coming from the first camera 31 and the second camera 32 and sends these images to PC 35. The image may be viewed on monitor 36. PC 35 may determine the grid frequency of the projected grid on the image received and compare the results to the original frequency of the grid used. The results will contain desired information about the surface topography. Alternatively, PC 35 may combine the two images revealing a moiré pattern which can be viewed on monitor 36.

In order to freeze rapid eye movements and to minimize thermal diffusion during the recording process, the illumination time can be reduced, for instance to about 1 ms. The flash thus created can be synchronized with the mid-IR cameras 31 and 32. In a specific embodiment two subsequent flashes can be synchronized with the first camera 31 and the second camera 32 subsequently, such that the first camera records an odd field and the second camera records an even field, which in term can be processed by the frame grabber 34 and the PC 35. The odd field may, for example, be comprised of the odd picture lines of the image, and the even field of the even picture lines. Combining both fields may then yield an image revealing a moiré pattern.

The second functionality of arrangement 14 of FIG. 1, recording of reference patterns underneath the corneal surface, such as pupil, iris and conjunctiva, is here performed by the addition of two ambient light sources 18 and 19 which may, according to the invention, provide near-IR ambient light for which the eye is at least partly transparent. For this purpose, recording of these references is performed by camera 11 which receives reflected near-IR light coming through lens 6, and is reflected by mirror 8 onto dichroic mirror 7. Dichroic mirror 7 transmits near-IR light which reaches camera 11 through lens 10.

The arrangement described above may be aligned, focused and magnified in order to project and receive suitable images at fixed distances at a fixed distance from the image receiving means. The arrangement may further comprise supporting means in which an object comprising a surface to be measured may be placed. The distance between the surface to be measured and the receiving means, after the object has been placed in front of the arrangement, must be close enough approximate to the fixed distance for which the arrangement may have been aligned, focused and magnified as mentioned above. For this purpose the supporting means or the arrangement as a whole my be arranged for calibrating the distance between the surface to be measured and the receiving means (this can be done by moving the object or moving the measuring device, as will be appreciated).

In order to determine whether the distance between the receiving means and the surface is equal to the distance for which the arrangement is able to project and receive suitable images, a triangulation method may be used as part of the invention.

Figure 3:
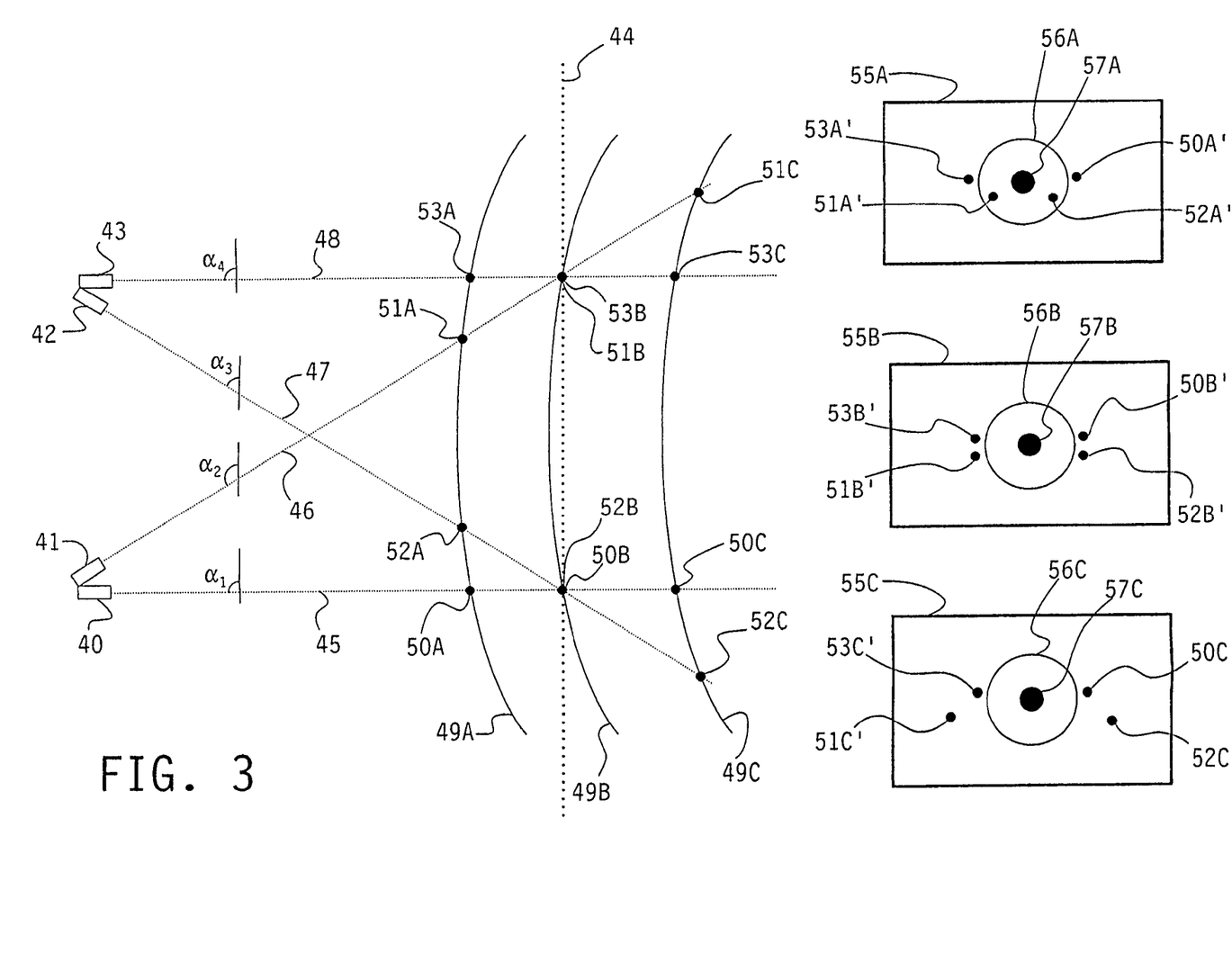
FIG. 3 is a schematic top view of the principle of the triangulation method of the present invention for adjusting the distance between the receiving units and the surface to be measured.

FIG. 3 schematically shows the principle of the triangulation method used for calibrating the distance between receiving means and surface. The arrangement is aligned, focused and magnified in order to project and receive a suitable image at the 'plane of focus' 44, indicated by a dotted line as the 'plane of focus' 44 is not physically present. Reference projection means 40-43 projecting a small spot as provided by near-IR lasers 21 and 22 in FIG. 1, project a plurality of reference points onto the surface to be measured. The reference projection means are arranged such that the points projected onto a imaginary projection plane in the 'plane of focus' 44 form a recognisable pattern, and in addition, the pattern formed by these points in any other plane is recognisably different.

The optical paths of the reference projection means 40-43 are shown as the dotted lines 45-48. The angle of projection of these optical paths relative to the plane of focus is indicated by $\alpha_1$ for path 45 of projection means 40, $\alpha_2$ for path 46 of projection means 41, $\alpha_3$ for path 47 of projection means 42, $\alpha_4$ for path 48 of projection means 43. A surface to be measured may be a corneal surface of an eye and is indicated in FIG. 3 as 49A, B and C, wherein A, B and C indicate three possible situations. The images received by receiving means (not shown) for the three situations are indicated by 55A, B and C. In all these images, 56(A, B and C) indicates the circumference of an iris and 57(A, B and C) is the pupil of the eye. The reference points are indicated by 50-53 A, B and C for each situation A, B and with an additional prime ("'") to indicate the representation of the reference on screen in images 55A, B and C.

The optimal situation, the situation wherein the surface 49B approximately coincides with the 'plane of focus' 44, at least close enough to acquire the desired accuracy in the results of the measurement, is here indicated by situation B. The optical paths 45 and 47 cross (but do not intersect) each other at different heights, as well as optical paths 48 and 46. Points 50B-53B recognisably form the corners of a rectangle, as can be seen in image 55B indicated by spots 50B', 52B', 51B' and 53B'.

Situation A shows the situation wherein the surface 49A is located in front of the 'plane of focus' 44, such that the distance between receiving means (not shown) and surface 49A is too small. In situation A, the reference points 50A, 52A, 51A and 53A do not form a rectangle as in the case of situation B. In this example the projection angles $\alpha_2$ and $\alpha_3$ of optical paths 46 and 47 respectively relative to the 'plane of focus' 44 are no straight angles (of approximately 90°), but are instead smaller and larger respectively. Therefore, moving surface 49A more to the front will cause reference points 51A and 52A to move closer to each other, while moving surface 49A backwards in the direction of the 'plane of focus' 44 will cause reference points 51A and 52A to move away from each other. In situation A, the image points 50A', 52A', 51A' and 53A' will form the corners of a trapezium in image 55A. An operator of the arrangement recognises this and may increase the distance between receiving means (not shown) and surface 49A, until the situation indicated by B is achieved.

Situation C shows a likewise situation as A, but in C the distance between the surface 49C and the receiving means (not shown) is too large, placing surface 49C behind the 'plane of focus' 44. Here, reference points 52C and 51C are further away from each other than 50C and 53C, such that in image 55C the reference points 50C', 51C', 52C' and 53C' form the corners of a trapezium. Similar as in situation A, an operator of the arrangement knows that the distance between surface 49C and receiving means (not shown) must be decreased.

As will be appreciated, other situations may be possible wherein it may be clear to an operator how to calibrate the distance between the receiving means and the object. In addition, it can likewise be visualised that a surface like 49 may be tilted, rotated or moved within the 'plane of focus' 44 (left, right, up, down or a combination thereof). For example, when the surface 49 may need to be tilted an asymmetric pattern may be seen in image 55.

A specific embodiment visualises (when the distance or orientation is calibrated correctly, as in situation B) the corners of a rectangle defining the surface that will be measured by the arrangement. This enables easy positioning of the arrangement relative to the object.

The arrangement described above, presented in FIG. 1 and FIG. 2, may be suitable for mid-IR radiation, but can easily be adapted for use with ultra violet (UV) projections or other colour (such as blue light). For instance, using a UV light source 1, a polarizer 17 may be placed in front of lens 6 and filters 27 and 28 may be replaced by polarization filters, of which the direction of polarization is perpendicular to the polarization direction of polarizer 17. The function of this set of polarizers is to remove light caused by specular reflection on the corneal surface 20. Additionally, it will be appreciated that using a UV light source 1, dichroic mirrors 7 and 8 are to be replaced by suitable dichroic mirrors.

Optionally, and especially for use in an arrangement suitable for projecting blue light, a fixation light source 9 can be placed in a straight line behind mirror 8 on the axis between mirror 8 and the corneal surface 20. The near-IR sources 17 and 18 as well as the near-IR projection lasers 21 and 22 not necessarily need to be replaced in case a different colour of light is used in the main projection source 1.

Figure 4:
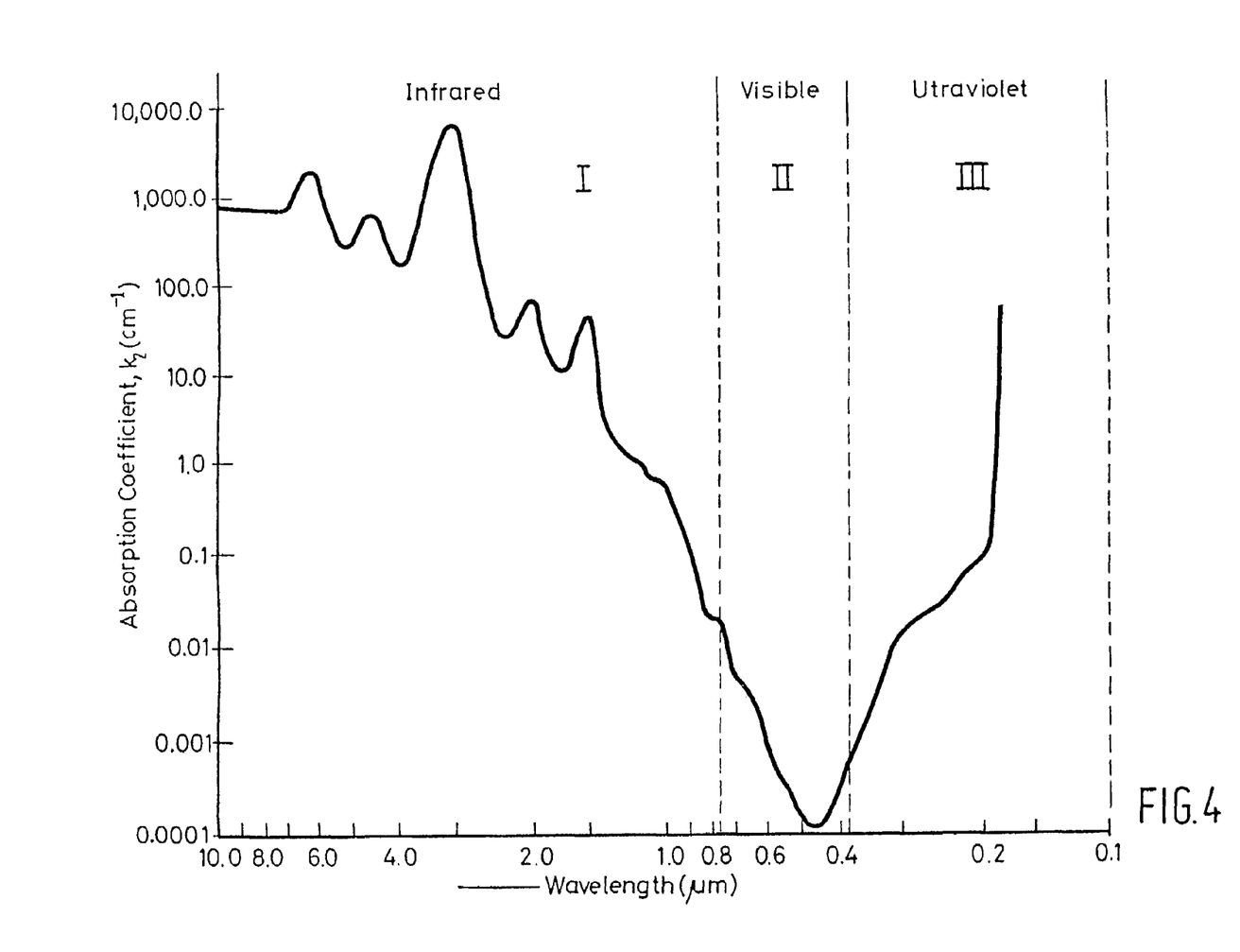
FIG. 4 is a double logarithmic diagram of the dependency of the absorption coefficient of sea water on the wave length of light (taken from "Sources of radiation—The Infrared & Electro-Optical Systems Handbook Vol. 1', G. J. Zissis (editor), SPIE, 1993, page 256)

FIG. 4, which is taken from "Sources of radiation—The Infrared & Electro-Optical Systems Handbook Vol. 1', G. J. Zissis (editor), SPIE, 1993, page 256, shows a diagram which depicts the dependency of the absorption coefficient k on the wavelength of light λ for sea water. The absorption coefficient of sea water is comparable to the absorption coefficient of the corneal tissue of the eye. As can be seen in the diagram, for visible light the region generally indicated with II (approximately between 0.4 and 0.8 μm) the eye is transparent. However, in the IR-region indicated with I, for wave length larger than 0.8 μm the absorption coefficient increases rapidly (note the double logarithmic scale), thus the eye is opaque for these frequencies around 0.8 μm, in the near-IR region, the eye is still partly transparent. In the ultra violet region, region III, with wave lengths smaller than approximately 0.4 μm, the corneal tissue starts to become opaque for frequencies smaller than 0.3 μm. However, for medical use and safety purposes, UV light with a wave length longer than 0.2 μm is not preferred, as it may permanently damage the tissue.

Figure 5:
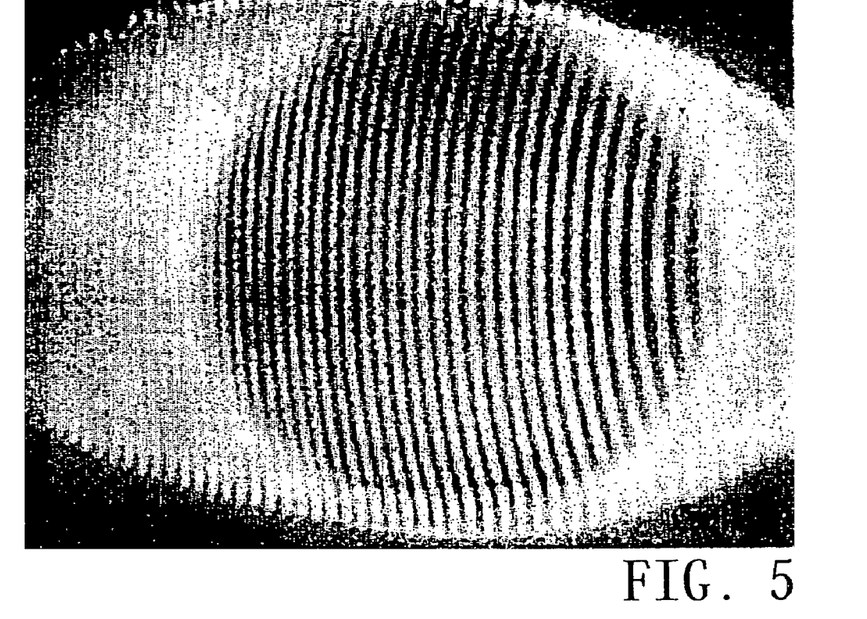
FIG. 5 shows a projected pattern on a corneal surface of which the topography is being measured.

FIG. 5 shows an image of a projected grid pattern on an eye surface in an arrangement as an example of the present invention. The image is received by receiving means that are placed under a different angle (with respect to their optical path to the surface) than the projection means.

Figure 6:
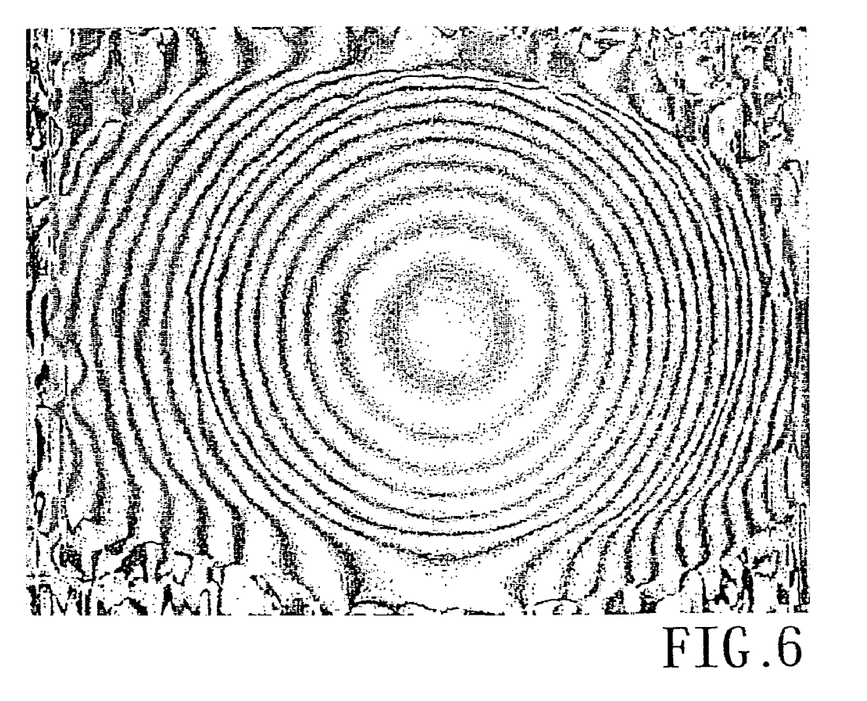
FIG. 6 shows an image acquired with fast Fourier analysis of the pattern of FIG. 5.

FIG. 6 shows a height topography map of an eye surface calculated by combination of the image of FIG. 5 with a similar image taken from a different angle (or with a different angle of projection to the surface). The images shown in FIG. 5 and 6 have been created as examples to explain the arrangement according to the present invention.

An arrangement according to the present invention is directed towards the method and arrangement disclosed in the amended claims. The arrangement described above, comprised of a single projection unit and two camera's may be embodied different. A possible amendment of the embodiment described is the use of a plurality of projection units for projecting one or more grid patterns onto the surface, or the use of a one or more receiving units (for example, one camera and two projection units).

It will be appreciated that numerous modifications and variations of the present invention are possible in the light of the above teachings. It is therefore understood that within the scope of the attached claims, the invention may be practised otherwise than specifically described herein.

The invention claimed is:

1. Method for performing measurements of a topography of a surface, such as the topography of an eye surface, wherein an image is projected onto said surface from at least one projection light source using projection means, wherein at least a fraction of light leaving the surface as a result of said projection is received using one or more receiving units, such as charged coupled device (CCD) based cameras, wherein measurement of said topography relates to surface mapping of said surface, wherein said topography of the surface is determined by analysis of said fraction of light leaving the surface, and wherein said fraction of light leaving the surface is comprised of light radiated by the surface due to thermal emission, characterised in that, said analysis for determining said topography of die surface is performed on said light radiated by the surface due to thermal emission.

2. Method according to claim 1, wherein at least one of the receiving units only receives said fraction of light leaving the surface during thermal excitation of the surface.

3. Method according to claim 1, wherein said fraction of the light leaving the surface further comprises reflected light that is reflected by the surface, and wherein said reflected light is removed before said analysis of said fraction of light leaving the surface.

4. Method according to claim 1, wherein the surface is at least part of the surface of a human or animal eye.

5. Method according to claim 1, wherein the image projected onto the surface is projected with light comprising a colour for which the surface is opaque.

6. Method according to claim 5, wherein said colour for which the surface is opaque corresponds to a colour of infrared (IR) light.

7. Method according to claim 6, wherein mid-IR light is used for projecting said image on the surface.

8. Method according lo claim 1, wherein said projection means flashes the image onto the surface, and wherein at least one of said receiving units is synchronised with said projection means.

9. Method according to claim 8, wherein said projection means projects the image during a series of flashes onto the surface, enabling determination of dynamics of the topography of the surface.

10. Method according to claim 8, wherein said flashing of said image is used to synchronise the at least one of said receiving units.

11. Method according to claim 1, wherein illumination of the surface by an ambient light source enables detection of structures on or underneath the surface using said one or more receiving units.

12. Method according to claim 11, wherein said ambient light source radiates light of a colour for which the surface is at least partly transparent.

13. Method according to claim 11, wherein the surface is at least part of an eye surface, and wherein the light radiated by said ambient light source is near-IR light.

14. Method according to claim 1, wherein a plurality of receiving units are used for receiving said fraction of light leaving the surface, wherein said receiving units are arranged for receiving a desired image of said fraction of light at a fixed distance from said surface, and wherein placing the surface at said fixed distance for receiving the desired image at least comprises the steps of:
  projecting a plurality of references onto the surface along an optical path using reference projection means, which references are projected such that at least one of the optical paths of said reference projection means is at an angle with at least one other of said optical paths of the reference projection means, and such that if the references are projected on the surface at said fixed distance to the receiving units, a recognisable pattern is formed on die surface by said references,
  adjusting the distance between surface and receiving units such that said references form said recognisable pattern on the surface.

15. Method according to claim 14, wherein near-IR light is used for projecting said references onto the surface.

16. Method according to claim 14, wherein the surface is an eye surface comprising a corneal surface, and wherein pupil; iris and conjunctiva are comprised underneath said surface, and wherein said more than one reference is projected onto a region of the conjunctiva outside a region of the corneal surface.

17. Method according to claim 1, wherein said image projected onto the surface is an interference pattern provided by any of a group of a grid, a slit, a double slit, an interferometer, and other means for creating an interference pattern.

18. Method according to claim 17, wherein said interference pattern used is a sinusoidal fringe pattern.

19. Method according to claim 1, wherein a Moire method, Fourier analysis methods or other profilometric methods are used for determining the topography of the surface.

20. Arrangement for performing measurements of the topography of a surface, such as topography of an eye surface, wherein measurement of said topography relates to surface mapping of said surface, said arrangement comprising projection means, which projection means comprise M least one projection light source for projecting an image onto the surface, further comprising one or more receiving units for receiving at least a fraction of light leaving the surface as a result of said projection, such as charged coupled device (CCD) based cameras, and means for analysis of said fraction of light leaving the surface for determining the topography of the surface, characterised in that, said analysis means for determining the topography of the surface are arranged for analysing light radiated by the surface due to thermal emission.

21. Arrangement according to claim 20, further comprising filtering means for filtering said fraction of light leaving said surface, said filtering means being arranged for transmission of light that is radiated by the surface due to thermal excitation.

22. Arrangement according to claim 20, wherein said projection means are arranged for flashing said image onto said surface.

23. Arrangement according to claim 22, comprising means for limiting a period of time for which at least one of said receiving units receives said fraction of light leaving the surface such that said period of time is approximately the duration of thermal emission as a result of said flashed image on said surface.

24. Arrangement according to claim 20, wherein said projection light source emits light of a colour for which the surface is opaque.

25. Arrangement according to claim 24, wherein said colour for which the surface is opaque corresponds to a colour of infrared (IR) light.

26. Arrangement according to claim 25, wherein mid-IR light is used for projecting said image on the surface.

27. Arrangement according to claim 20, comprising means for synchronising said receiving units with said projection means.

28. Arrangement according to claim 20, further comprising an ambient light source and means for detecting references on said surface.

29. Arrangement according to claim 28, wherein said ambient light source comprises a near-IR light source.

30. Arrangement according to claim 20, comprising a plurality of receiving units, and further comprising means for projecting more than one reference onto the surface, and means for constructing a composite image from images received by said receiving units.

31. Arrangement according to claim 20, wherein said projecting means comprises means for projecting an interference pattern onto said surface.

* * * * *

UNITED STATES PATENT AND TRADEMARK OFFICE
CERTIFICATE OF CORRECTION

| | | |
|---|---|---|
| PATENT NO. | : 7,431,458 B2 | Page 1 of 1 |
| APPLICATION NO. | : 10/524769 | |
| DATED | : October 7, 2008 | |
| INVENTOR(S) | : Franciscus Hermanus M Jongsma et al. | |

It is certified that error appears in the above-identified patent and that said Letters Patent is hereby corrected as shown below:

On the Title Page

Please add item (30) as follows:

-- (30) Foreign Application Priority Data

August 16, 2002 (EPO).............02078409.6 --.

Signed and Sealed this

Nineteenth Day of May, 2009

JOHN DOLL
*Acting Director of the United States Patent and Trademark Office*